US010448900B2

(12) United States Patent
Guazzi

(10) Patent No.: US 10,448,900 B2
(45) Date of Patent: Oct. 22, 2019

(54) METHOD AND APPARATUS FOR PHYSIOLOGICAL MONITORING

(71) Applicant: OXEHEALTH LIMITED, Oxford, Oxfordshire (GB)

(72) Inventor: Alessandro Guazzi, Oxford (GB)

(73) Assignee: OXEHEALTH LIMITED, Oxford (GB)

( * ) Notice: Subject to any disclaimer, the term of this patent is extended or adjusted under 35 U.S.C. 154(b) by 327 days.

(21) Appl. No.: 15/533,818

(22) PCT Filed: Dec. 8, 2015

(86) PCT No.: PCT/GB2015/053754
§ 371 (c)(1),
(2) Date: Jun. 7, 2017

(87) PCT Pub. No.: WO2016/092290
PCT Pub. Date: Jun. 16, 2016

(65) Prior Publication Data
US 2017/0347967 A1 Dec. 7, 2017

(30) Foreign Application Priority Data
Dec. 8, 2014 (GB) .................................. 1421785.5

(51) Int. Cl.
*A61B 5/00* (2006.01)
*A61B 5/0205* (2006.01)
(Continued)

(52) U.S. Cl.
CPC .......... *A61B 5/7278* (2013.01); *A61B 5/0075* (2013.01); *A61B 5/0077* (2013.01);
(Continued)

(58) Field of Classification Search
USPC ........................................................ 382/128
See application file for complete search history.

(56) References Cited

U.S. PATENT DOCUMENTS 9,615,749 B2 * 4/2017 Clifton ................ A61B 5/0205
9,659,229 B2 * 5/2017 Clifton ................ A61B 5/0205
(Continued)

FOREIGN PATENT DOCUMENTS

WO  WO-2009/016334 A1  2/2009
WO  WO-2011080189 A1  7/2011
(Continued)

OTHER PUBLICATIONS

International Search Report and Written Opinion of the International Searching Authority issued in PCT/GB2015/053754, dated Feb. 12, 2016. ISA/EPO.
(Continued)

*Primary Examiner* — Ishrat I Sherali
(74) *Attorney, Agent, or Firm* — Harness, Dickey & Pierce, P.L.C.

(57) ABSTRACT

Autoregressive modelling is used to identify periodic physiological signals such as heart rate or breathing rate in an image of a subject. The color channels of a video signal are windowed and normalised by dividing each signal by its mean. The ratios of the normalised channels to each other are found and principal component analyses conducted on the ratio signals. The most periodic of the principal components is selected and autoregressive models of one or more different orders are fitted to the selected component. Poles of the fitted autoregressive models of different orders are taken and pure sinusoids corresponding to the frequency of each pole are generated and their cross-correlation with the original component is found. Whichever pole corresponds to the sinusoid with the maximum cross-correlation is selected as the best estimate of the frequency of periodic physiological information in the original video signal. The method may be used in a patient monitor or in a webcam-enabled device such as a tablet computer or smart phone.

25 Claims, 8 Drawing Sheets

(51) Int. Cl.
*A61B 5/026* (2006.01)
*A61B 5/0295* (2006.01)
*A61B 5/08* (2006.01)
*G06K 9/46* (2006.01)
*A61B 5/024* (2006.01)
*A61B 5/11* (2006.01)
*A61B 5/113* (2006.01)

(52) U.S. Cl.
CPC .......... *A61B 5/0205* (2013.01); *A61B 5/0261* (2013.01); *A61B 5/0295* (2013.01); *A61B 5/6898* (2013.01); *A61B 5/7246* (2013.01); *A61B 5/7253* (2013.01); *A61B 5/7257* (2013.01); *A61B 5/02427* (2013.01); *A61B 5/0816* (2013.01); *A61B 5/1102* (2013.01); *A61B 5/113* (2013.01); *A61B 5/1128* (2013.01); *A61B 5/7203* (2013.01); *A61B 2562/0233* (2013.01); *A61B 2576/00* (2013.01); *G06K 9/4652* (2013.01)

(56) References Cited

U.S. PATENT DOCUMENTS

| | | | |
|---|---|---|---|
| 2010/0016693 | A1 | 1/2010 | Addison et al. |
| 2010/0204550 | A1* | 8/2010 | Heneghan ............... G16H 50/30 600/301 |
| 2010/0298730 | A1* | 11/2010 | Tarassenko .......... A61B 5/0816 600/529 |
| 2014/0073954 | A1 | 3/2014 | Engelbrecht et al. |
| 2015/0223701 | A1* | 8/2015 | Ghaemi ................. G16H 40/67 600/430 |
| 2015/0379370 | A1* | 12/2015 | Clifton ................. A61B 5/0205 382/128 |
| 2016/0007865 | A1 | 1/2016 | Sakata et al. |
| 2019/0183452 | A1* | 6/2019 | Nair ....................... A61B 8/085 |

FOREIGN PATENT DOCUMENTS

| | | |
|---|---|---|
| WO | WO-13027027 A2 | 2/2013 |
| WO | WO-2014009111 A1 | 1/2014 |
| WO | WO-2014/125250 A1 | 8/2014 |

OTHER PUBLICATIONS

GB Search Report of the Intellectual Property Office under Section 17 issued in application No. GB 1421785.5, dated Jun. 8, 2015.

Tarassenko, L. et al: "Non-contact video-based vital sign monitoring using ambient light and auto-regressive models", Physiological Measurement, Institute of Physics Publishing, Bristol, GB, vol. 35, No. 5, Mar. 28, 2014 (Mar. 28, 2014), pp. 807-831.

Nam, Yunyoung et al: "Respiratory Rate Estimation from the Built-in Cameras of Smartphones and Tablets", Annals of Biomedical Engineering, vol. 42, No. 4, Nov. 23, 2013 (Nov. 23, 2013), pp. 885-898.

Martn-Martinez, Diego et al: "Stochastic Modeling of the PPG Signal: A Synthesis-by-Analysis Approach With Applications", IEEE Transactions on Biomedical Engineering, IEEE Service Center, Piscataway, NJ, USA, vol. 60, No. 9, Sep. 1, 2013 (Sep. 1, 2013), pp. 2432-2441.

Martin-Martinez, D. et al: "Cardiovascular signal reconstruction based on shape modelling and non-stationary temporal modelling", 2006 14th European Signal Processing Conference, Jan. 1, 2012 (Jan. 1, 2012), pp. 1826-1830.

Haan, Gerard de et al., "Robust Pulse Rate From Chrominance-Based rPPG", IEEE Transactions on Biomedical Engineering, vol. 60, No. 10, Oct. 2013.

Feng, Litong et al., "Motion Artifacts Suppression for Remote Imaging Photoplethysmography", Proceedings of the 19$^{th}$ International Conference on Digital Signal Processing, Aug. 20-23, 2014.

* cited by examiner

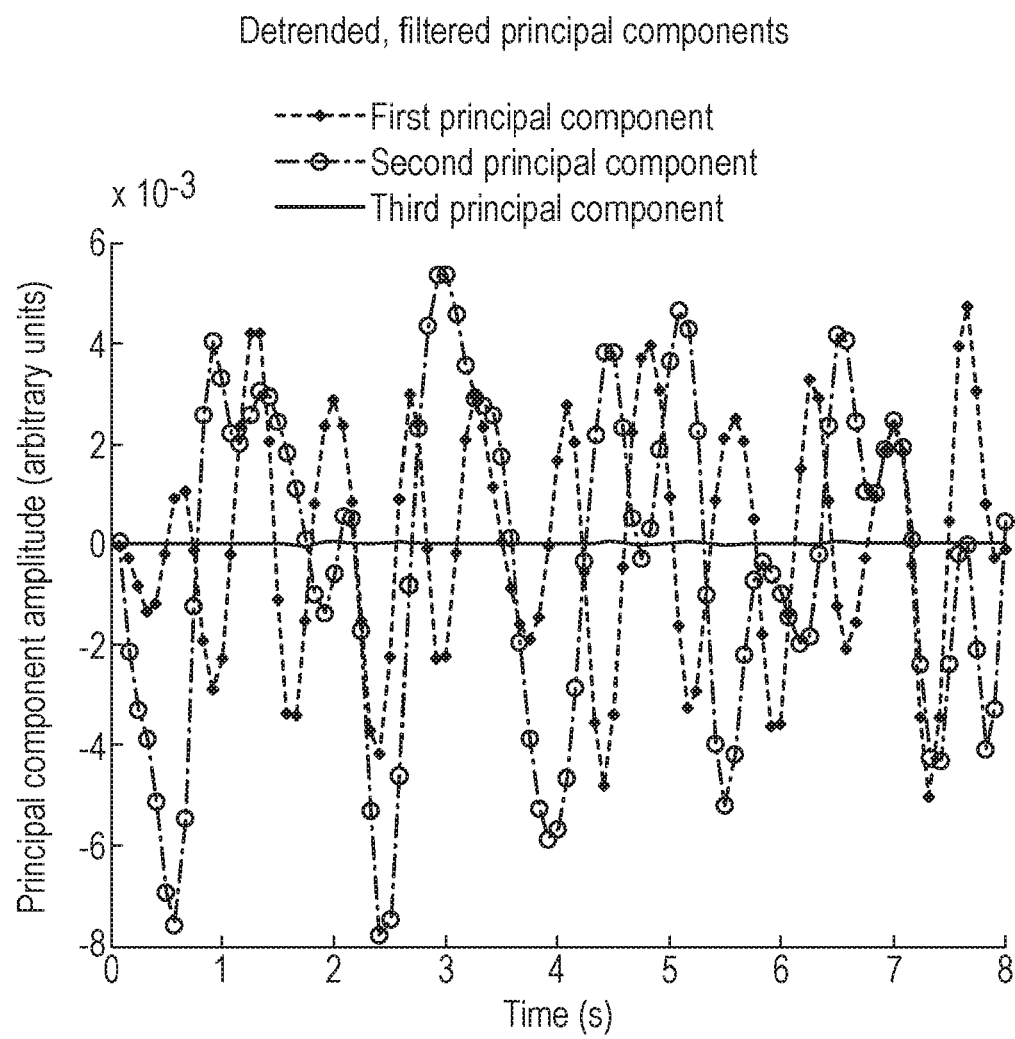

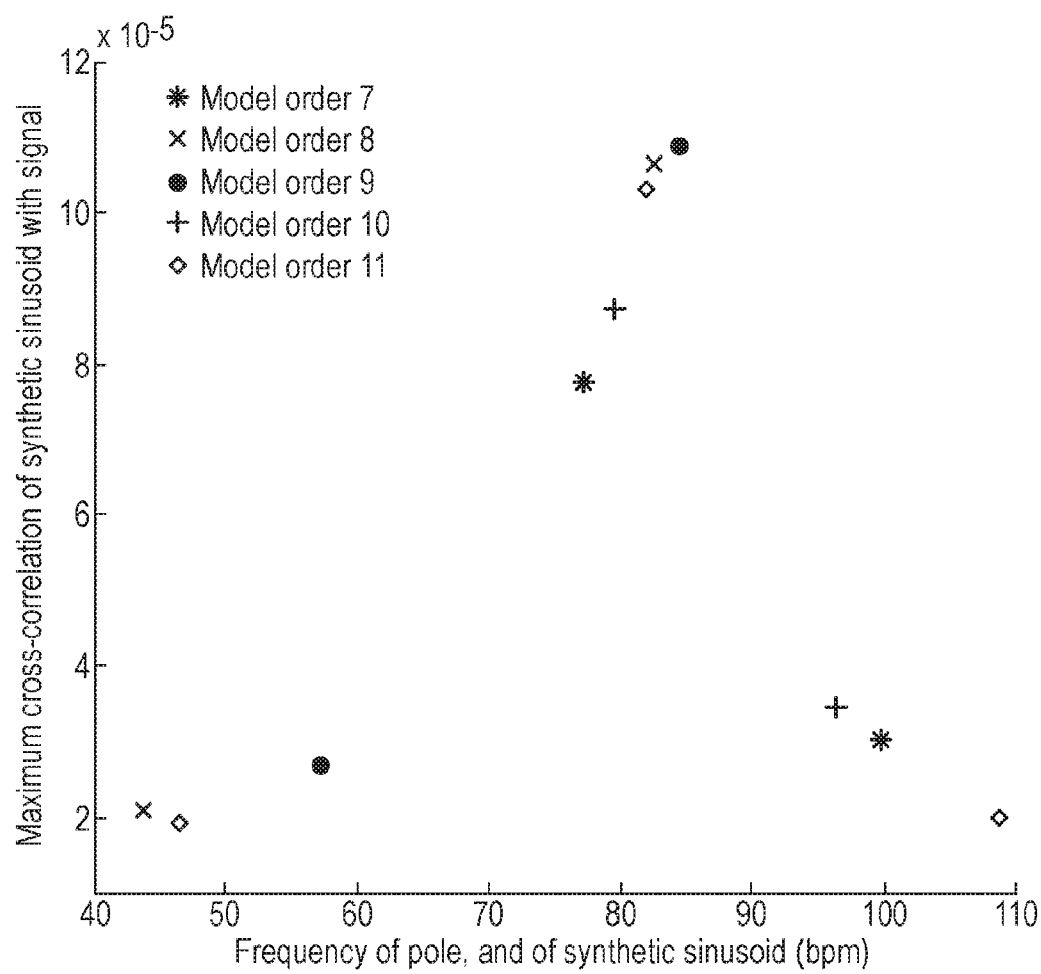

METHOD AND APPARATUS FOR PHYSIOLOGICAL MONITORING

CROSS REFERENCE TO RELATED APPLICATIONS

This application is a U.S, National Phase Application under 35 U.S.C. 371 of International Application No, PCT/GB2015/053754 filed on Dec. 8, 2015 and published as WO 2016/092290 A1 on Jun. 18, 2016. This application is based on and claims the benefit of priority from Great Britain Patent Application No. 1421785.5 filed Dec. 8, 2014. The entire disclosures of all of the above applications are incorporated herein by reference.

The present invention relates to the remote monitoring of a human or animal subject to detect periodic physiological signals such as the heart rate or breathing rate.

The detection of periodic physiological signals, such as heart rate or breathing (respiration) rate, of a subject is a vital part of patient monitoring. Traditionally contact sensors have been used so that the heart rate can be detected by means of an ECG monitor or PPG finger probe and the breathing rate can either be derived from the ECG or PPG signals or measured directly by impedance pneumography. A PPG finger probe also gives the blood oxygen saturation ($SpO_2$). However contact-based sensors are not ideal for monitoring patients who move or are mobile, or for long-term monitoring. More recently, therefore, proposals have been made for non-contact monitoring. One such proposal is to derive measures of the heart rate and breathing rate from a photoplethysmographic image (PPGi). As discussed in the applicant's own published patent application WO-A2-2013/027027, a video image of the patient's skin can be analysed to detect the variation in transmittance or reflectance of light at certain wavelengths as the volume of blood in the skin capillaries varies with the cardiac cycle. Although invisible to normal sight, the skin can effectively be regarded as pulsing more red and less red with each heart beat. This change can be detected in a standard colour video image of the skin taken with a normal video camera such as a webcam. WO-A2-2013/027027 explains how the heart rate and breathing rate can be derived from such a colour video signal.

FIG. 1 of the accompanying drawings schematically illustrates the PPGi analysis process. In step 100 a standard video signal with 3 colour channels (red, green, blue) is received, for example from a webcam of the type found in a tablet computer or smartphone, and in step 101 a region of interest positioned over bare skin in the image is defined and for each of the three colour channels, at each time point, the mean of the intensities over that region of interest is obtained. This gives a time-series of values for each colour, each value being the mean intensity for that colour over the whole region of interest. In step 102 the green channel is selected, as this has the most cardiac information. In step 103 the signal is divided into short overlapping time windows. Each time window is 15 seconds long and the window slides by one second at a time. Ultimately a heart rate or breathing rate estimate will be outputted for each window, thus one estimate will be outputted every second. In step 104 the time series in each window is detrended (by removing the best fit straight line from the data) and then filtered, e.g. using a zero-phase finite impulse response (FIR) filter of order 30, with cut-offs between 0.7 Hz and 2 Hz, corresponding to heart rates of 42 beats per minute and 120 beats per minute respectively the usual range of adult resting heart rates.

The aim is then to spectrally analyse the signal to find a periodic variation corresponding to the heart rate (or breathing rate). In this prior art this is done in steps 105 to 107 by fitting autoregressive models to the signal. Thus in step 105 several autoregressive models of different orders are fitted to the signal (for example orders 8 to 20). As explained in WO-A2-2013/027027 autoregressive modelling can be regarded as filtering with an all-pole infinite impulse response filter (IIR) with a white noise input in which the number of poles is determined by the model order. In spectral analysis it is the properties of these poles which are of interest. The poles can be viewed as points lying in the complex plane in an area conscribed by the unit circle, having a phase angle that is related to a pure frequency component of the signal and a magnitude that is related to the strength of that component. The analysis of the signals in step 105 generates, for each model order, several poles representing different frequencies present in the signal. In order to find which pole represents the heart rate (or breathing rate) poles representing frequencies outside the allowed range for heart rate (or breathing rate) can be ignored and then the pole with the largest magnitude and/or lowest frequency, can be selected. The phase angle of the selected pole corresponds to a particular frequency assumed to correspond to the heart rate estimate from that model. The estimates from each of the different model orders are taken and averaged in step 107, and in step 108 the heart rate estimate based on that average is output.

It will be appreciated that because the frequency estimate from each model order is based on the selected pole, the selection of that pole is of critical importance. However it can be difficult, in practice, to select the correct poles from the fitted autoregressive models. Selection of the wrong pole will result in an erroneous frequency estimate. Further, although it is anticipated that remote monitoring will be better than contact-based sensors in the case of moving subjects, movement of the subject in the video image can create movement artefacts which make signal processing difficult. It is very well known from video encoding technologies how to track parts of a video image from one frame to the next, and such tracking can be used to keep the region of interest on the skin of the subject. Nevertheless it would be useful to improve the motion compensation in order to improve the signal before spectral analysis. PPGi analysis can also be sensitive to lighting changes and it would also be useful to improve the robustness of the method to such changes, e.g. flicker in ceiling lights.

One aspect of the present invention provides a method of detecting the frequency of a periodic physiological signal of a subject from a video image of the subject, comprising the steps of: fitting autoregressive models of one or more orders to a signal derived from the video image to detect spectral components in the signal; for each spectral component generating a synthetic signal of the same frequency and calculating its similarity in the time domain with the signal derived from the video image; outputting as the physiological signal frequency the frequency of the synthetic signal with the maximum similarity with the signal derived from the video image.

Thus with the present invention the pole selection from the fitted autoregressive model or models is conducted by a time domain analysis of the frequency that each pole represents with the signal to which the autoregressive model was fitted. Thus the spectral analysis using the autoregressive model is performed in the frequency domain, but the selection of the resulting pole is performed by reference back to the time domain. The spectral component (pole)

which most closely represents the desired periodic physiological signal will have the highest cross-correlation in the time domain with the original signal.

The measure of similarity may be the cross-correlation. Any of the standard cross-correlation techniques well-known from signal analysis can be used.

The synthetic signal is preferably sinusoidal.

The method may further comprise the step of defining a similarity threshold and inhibiting the outputting step if the similarity of the synthetic signal with the maximum similarity with the selected ratio signal is below the threshold. This avoids outputting poor estimates of the frequency of the physiological signal.

The signal derived from the video image may be a single colour channel of video source data, and the colour channel may be visible or infra-red (IR). The signal derived from the video image can be a ratio of two colour channels of video source data, the channels being in the visible or IR region.

Alternatively the signal derived from the video image can be a sequence of co-ordinates obtained by tracking movement in the image, e.g. a sequence of co-ordinates of a physical feature or region of high contrast being tracked.

The signal derived from the video image is derived by the following steps: receiving multiple colour channels of video source data representing said video image, each channel comprising a time series of intensity data for that colour channel; for each different pairing of the colour channels calculating the ratio of the intensity at each time point in a first of the pairing to the intensity at the same time point in the second of the pairing to produce multiple ratio signals; performing source separation on the ratio signals and selecting the output component which is most periodic. The autoregressive models are fitted not to the colour channel signals themselves but to the most periodic component in the ratio signals resulting from dividing the signal in one colour channel by the signal in another. Preferably the ratios are the red to green ratio, the red to blue ratio, and the green to blue ratio (or their reciprocals). Each of the colour channels can be normalised by dividing by its mean value before the ratio calculation. Because changes in lighting of the image or movement of the subject tend to affect all channels at once, taking the ratios of the colour channels eliminates to some degree the effect of such lighting changes or movement.

It is possible to generate a synthetic time-domain signal for each spectral component from each model and calculate its cross-correlation with the signal to which the autoregressive model was fitted, or alternatively only poles in a selected frequency range (e.g. the allowed range for the physiological signal of interest) can be selected, or only the dominant pole (i.e. pole with the greatest magnitude) from each model is used. Choosing only the dominant pole of each model speeds-up the signal processing.

In an alternative embodiment the signal derived from the video image can be derived by the following steps: receiving multiple sequences of co-ordinates of one or more physical features being tracked; performing source separation on the sequences and selecting the output component which is most periodic.

The source separation step mentioned above may be by Principal Component Analysis. The selection of the most periodic output component is preferably by selecting the component having the greatest peakiness of frequency spectrum. In the method the three ratio signals resulting from dividing one of the colour channel signals by another are subject to principal component analysis and whichever component is the most periodic is selected as the signal for autoregressive analysis for that window. The selection as "most periodic" can be achieved by selecting the signal with the peakiest spectrum within the physiological frequency range of interest, i.e. which has a peak with the highest power as a proportion of the power at all frequencies. The selection of the most periodic of the signals results in a further improvement in movement compensation. Other methods of choosing the most periodic signal, such as analysis of the autocorrelation of each signal, can be used.

Autoregressive models of order 8-20, more preferably 7 to 11, can be fitted to the signal derived from the video image.

Preferably a synthetic signal is generated corresponding to the frequency of only the dominant spectral component for each order model.

Each colour channel is preferably normalised by dividing by its mean before the step of calculating the ratio.

The signal derived from the video image is preferably temporally windowed, e.g. into overlapping windows, for example from 4-30 seconds long with an overlap from 0.5 to 10 seconds.

The video source data may be a time series of intensity data for each colour channel for a region of interest defined in the video image. The region of interest is preferably on the skin of the subject and the video source data is a photoplethysmographic image. The region of interest may include a periodically moving part of subject.

The periodic physiological signal may be the heart rate or respiration rate of the subject.

The invention can be embodied as a computer program comprising program code means for executing the method on a computer system. Alternatively it can be incorporated into a dedicated patient monitor.

Thus another aspect of the invention provides apparatus for detecting the frequency of a periodic physiological signal of a subject from a video image of the subject comprising: an input for receiving one or more colour channels of video source data representing said video image, each channel comprising a time series of intensity data for that colour channel; a processor for processing video source data; the processor being configured to execute the steps of the method above; the apparatus further comprising an output to output as the physiological signal frequency the frequency of the synthetic signal with the maximum cross-correlation with the selected ratio signal. As above the colour channel may be visible or IR.

The invention will be further described by way of example with reference to the accompanying drawings in which:—

Figure 3A:
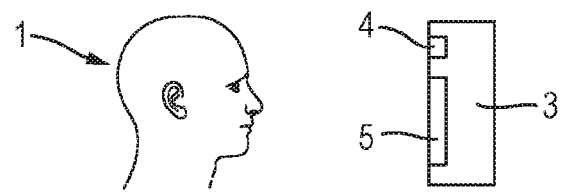
Figure 4A:
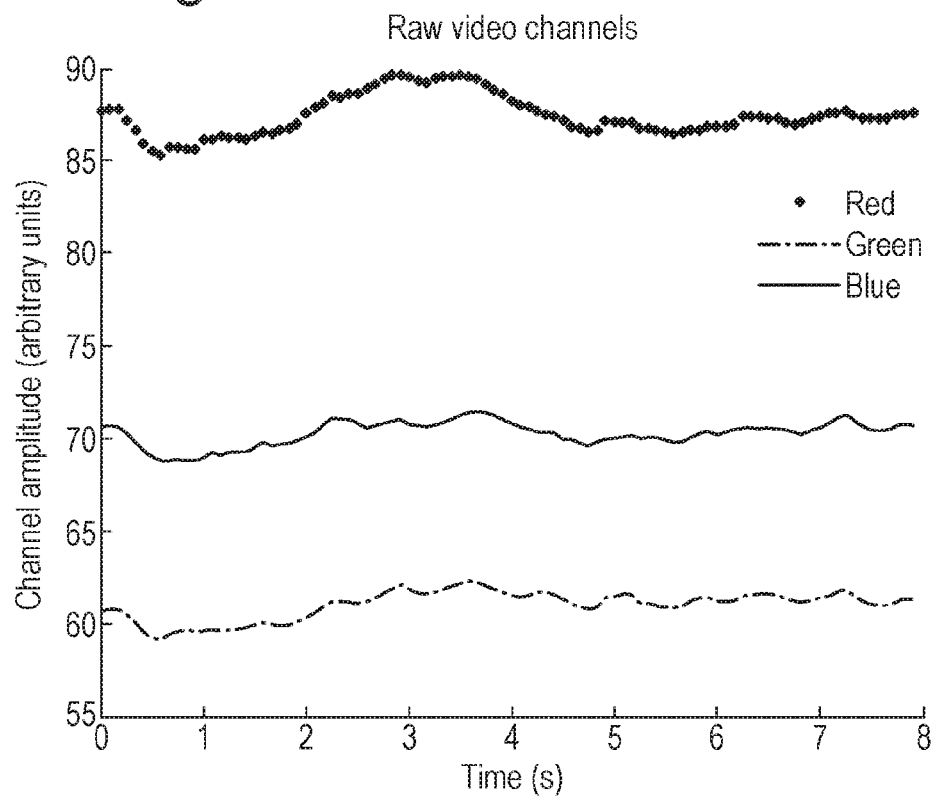
Figure 4B:
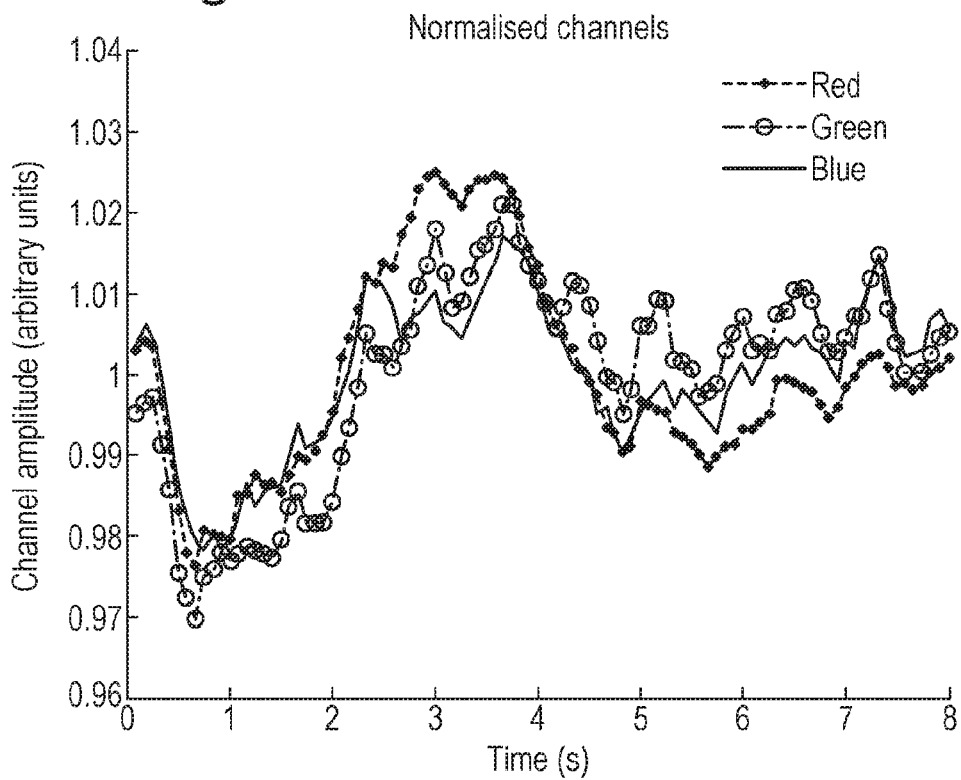
Figure 4C:
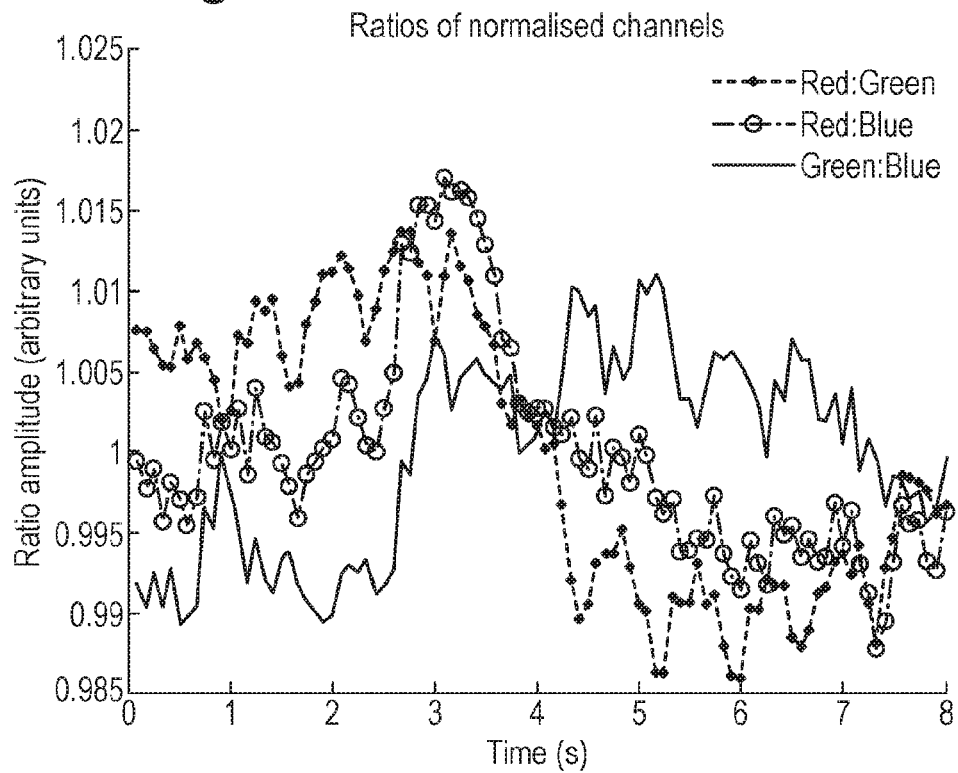
Figure 4D:
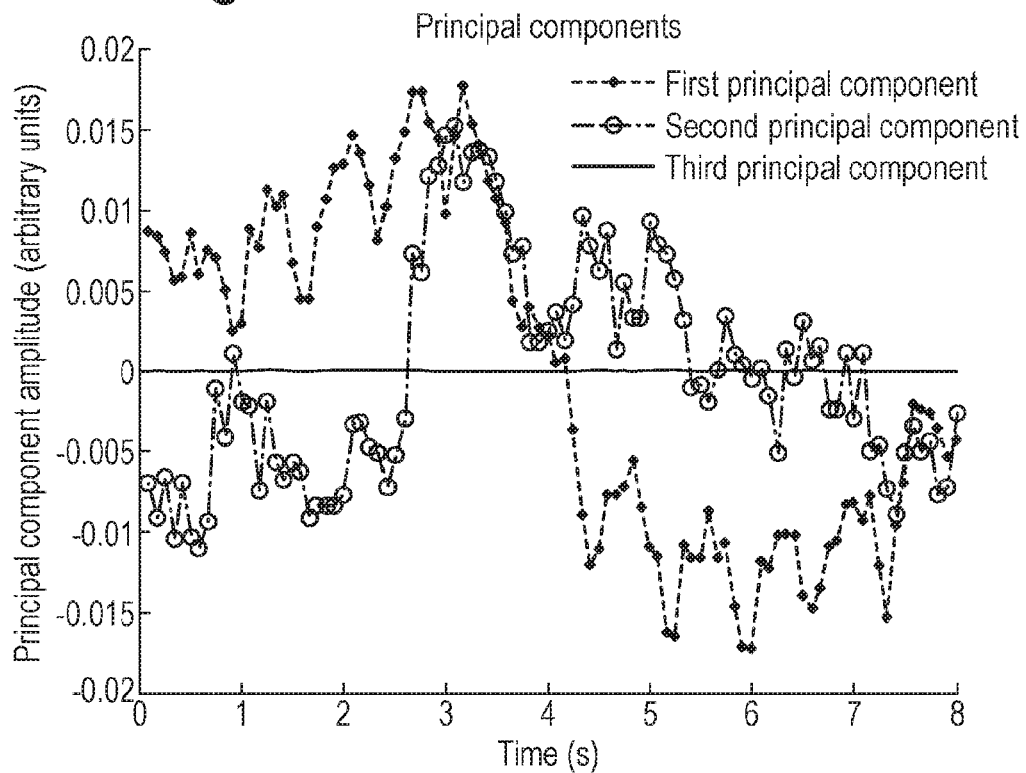
Figure 4F:
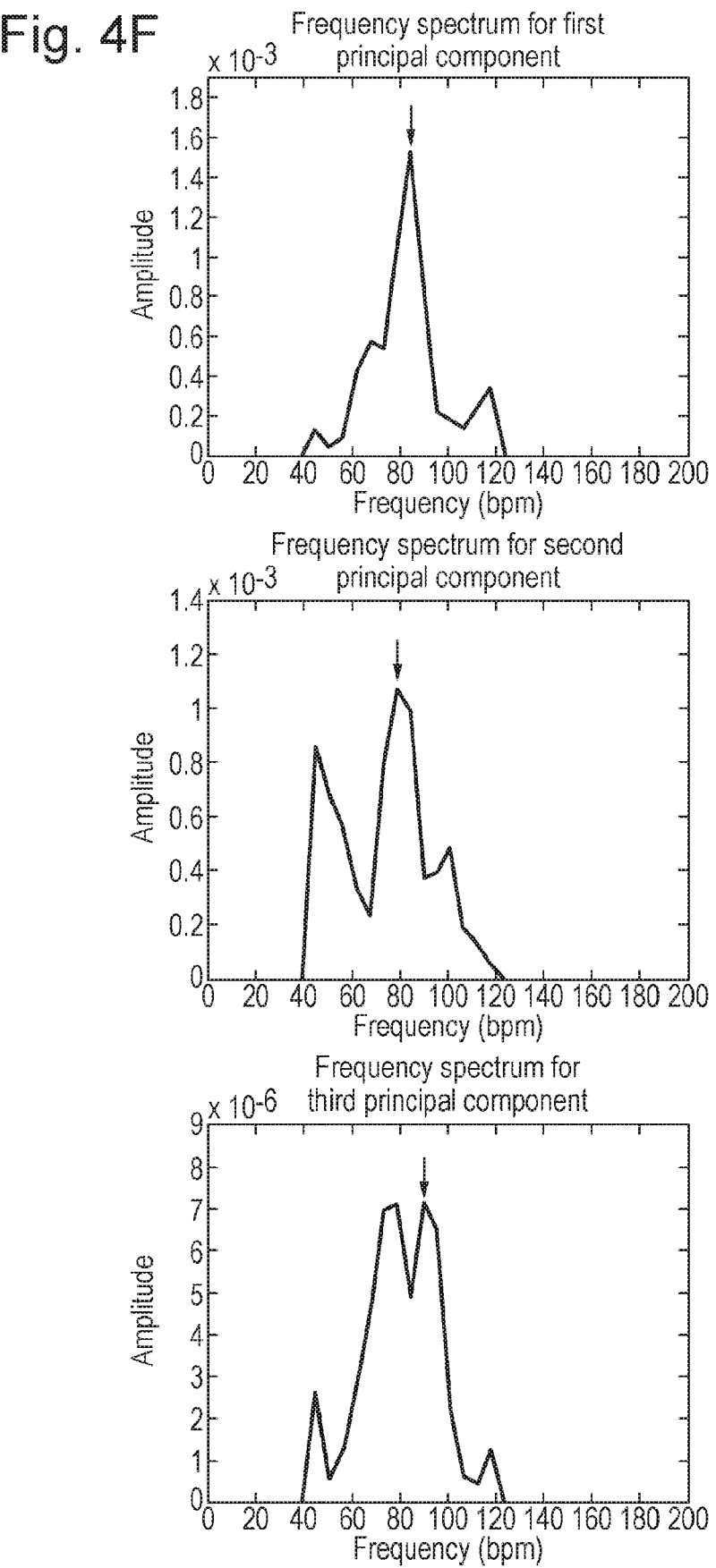

FIGS. 3A, B and C schematically illustrate apparatus and a video image in one embodiment of the invention; and FIGS. 4A, B, C, D, E, F and G illustrate data from steps in the method for an example in which heart rate is estimated.

FIG. 3A schematically illustrates in side view a subject 1 facing a device 3 which is integrally provided with a video camera such as a webcam 4 and a display screen 5. The device 3 can be a tablet or notebook computer, a mobile telephone (smart phone) or a dedicated patient monitor or other electronic equipment provided with a video camera 4. As will be explained below, device 3 is loaded with a software application which obtains the red, green and blue video output from the video camera 4 and analyses it to obtain a measurement of one or more of the subject's periodic vital signs such as the heart rate or breathing rate. These measurements are stored and displayed to the patient (on demand) and may also be sent by a network or Internet connection (not shown) to a remote server (not shown). The despatch and storage of signals and/or measurements on the remote server would allow automatic analysis and alerting, as well as allowing remote clinicians to review the subject's condition and, if necessary, advise the patient either via a messaging application within the software application itself or by other communication channels such as conventional messaging or telephones.

Figure 3B:
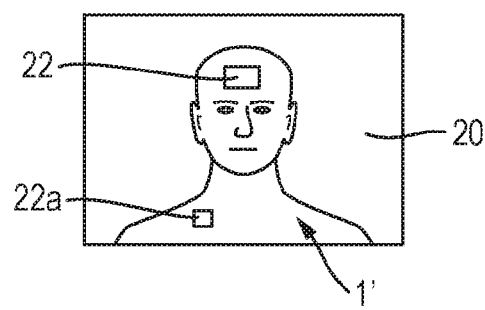
Figure 3C:
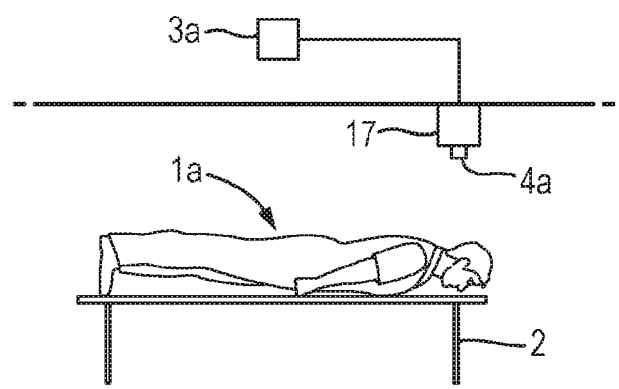

FIG. 3C illustrates an embodiment of the monitoring system intended for monitoring patients in hospitals. As illustrated, the monitor includes a video camera 4a mounted above the patient 1a for example on the ceiling or a frame 17, where it can view the patient 1a while the patient is on a bed 2. The output from the video camera 4a is supplied to a processing unit 3a via a conventional wired or wireless connection.

FIG. 3B illustrates schematically the image obtained by the video camera 4. In general the image will contain an image 1' of the subject 1 and a background 20. One or more regions of interest (ROIs) 22 are defined in the image 1'. For the detection of a PPGi signal the region of interest 22 needs to be on an area of skin, e.g. the face of the subject. A breathing rate signal can also be obtained by looking for periodic movement of the body of the subject, e.g. the chest, or movement of something in contact with the subject, e.g. pillow or bedclothes, in which case the region of interest 22a can be defined on the chest. Conventional recognition and tracking algorithms can be used to find and track a suitable region 22, 22a in the image 1'. The region of interest 22, 22a can also be set initially by an operator or clinician, and then maintained automatically by tracking.

Figure 2:
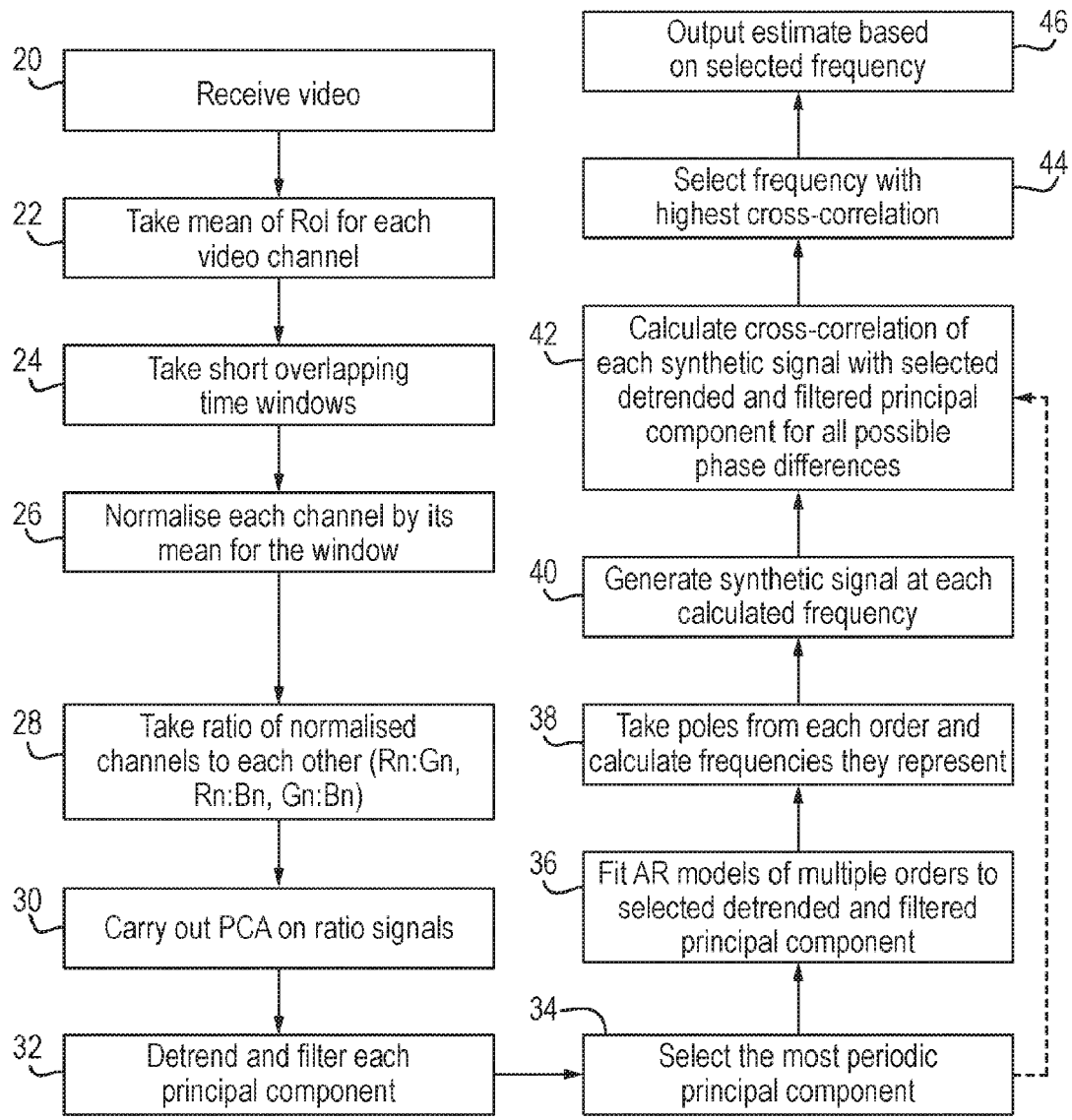
FIG. 2 is a flowchart explaining a method of physiological signal analysis according to an embodiment of the present invention.

FIG. 2 sets out the process for analysing the signals from the video camera 4 to detect the frequency of a periodic physiological signal in the video image 1'. This may be a PPGi signal taken from a region of interest on the skin or a periodic movement signal obtained from, for example, the region of interest 22a defined on the chest. The movement signal can be the periodic variation in the coordinates of a tracked feature in the image. In step 20 the video signal consisting of red, green and blue channels is received. The signal will consist of one spatial frame of data for each time point (the frame rate varies with the application but can be 12 or 24 frames per second). In step 22 a representative intensity for the region of interest in each frame for each of the three colour channels is obtained. This may, for example, be the mean intensity of each colour taken over the whole region of interest (i.e. the mean of all the red pixel values in the region of interest, the mean of all the green pixel values in the region of interest and the mean of all the blue pixel values in the region of interest).

$$\overline{R^{ROI}} = \frac{\sum_{ROI} \text{Red pixel intensities}}{\text{number of red pixels in } ROI}$$

$$\overline{G^{ROI}} = \frac{\sum_{ROI} \text{Green pixel intensities}}{\text{number of green pixels in } ROI}$$

$$\overline{B^{ROI}} = \frac{\sum_{ROI} \text{Blue pixel intensities}}{\text{number of blue pixels in } ROI}$$

However alternatively the mode of the distribution of intensities for each of the three colour channels within the region of interest can be used, or another representative intensity for each channel in the region of interest.

Once the representative intensity for each colour channel for each frame has been obtained, a time series of these intensities is assembled for a series of frames in a time window of, for example, 15 seconds. The length of the time window can be different, for example from 8 seconds to 1 minute. Each window overlaps its neighbour by a small time period, for example 1 second, though different overlaps, for example from 0.5 seconds to 5 seconds are usable.

$$\overline{R_{t1}^{ROI}} \ldots \overline{R_{twindow}^{ROI}} \; \overline{G_{t1}^{ROI}} \ldots \overline{G_{twindow}^{ROI}} \; \overline{B_{t1}^{ROI}} \ldots \overline{B_{twindow}^{ROI}}$$

In step 26 the signal values for each channel in each window are normalised by dividing each value by the mean of the representative intensities for that colour channel over that time window.

$$n_R(t) = \frac{\overline{R_{t1}^{ROI}}}{\mu_{window}^{Red}} \ldots \frac{\overline{R_{twindow}^{ROI}}}{\mu_{window}^{Red}}; n_G(t) = \frac{\overline{G_{t1}^{ROI}}}{\mu_{window}^{green}} \ldots \frac{\overline{G_{twindow}^{ROI}}}{\mu_{window}^{green}};$$

$$n_B(t) = \frac{\overline{B_{t1}^{ROI}}}{\mu_{window}^{blue}} \ldots \frac{\overline{B_{twindow}^{ROI}}}{\mu_{window}^{blue}};$$

In step 28 the ratio of the normalised channels to each other is obtained. That is to say for each time point in the sequence, the normalised value for the red channel is divided by the normalised value for the green channel, the normalised value for the red channel is divided by the normalised value for the blue channel and the normalised value for the green channel is divided by the normalised value for the blue channel. This generates three different ratio signals consisting of a ratio value for each of the frames (each time point) in the window.

$$R1(t) = \frac{n_R(t)}{n_G(t)}, R2(t) = \frac{n_R(t)}{n_B(t)}, R3(t) = \frac{n_G(t)}{n_B(t)}$$

For each sequence of ratios Principal Component Analysis (PCA) is carried out in step 30 and the output components are detrended and filtered (e.g. by a bandpass digital filter whose pass band is the range of physiological signal frequencies) in step 32.

Then in step 34 whichever of the detrended and filtered components is most periodic is judged. This is achieved in this embodiment by selecting the signal with the peakiest spectrum, i.e. that which has the peak with the highest power as a proportion of the total power at all physiologically-possible frequencies. For example, the criterion can be to be maximise the value of:—

$$\max \text{peak}(F)^2/\text{area}(F)$$

Where F is the signal in the frequency domain, max peak (F) is the peak power, and area (F) is the area underneath the power spectral density curve in the frequency range where the physiological signal may exist. This can easily be calculated from a Fast Fourier Transform of the detrended and filtered PCA output.

As a result whichever of the three components is regarded as most periodic is then the subject of autoregressive modelling in step 36 by fitting autoregressive models of multiple orders to the sequence of values for that window. In this embodiment AR models of order 7-11 are fitted to each sequence. However the order and number of model orders can be varied for different applications.

Figure 1:
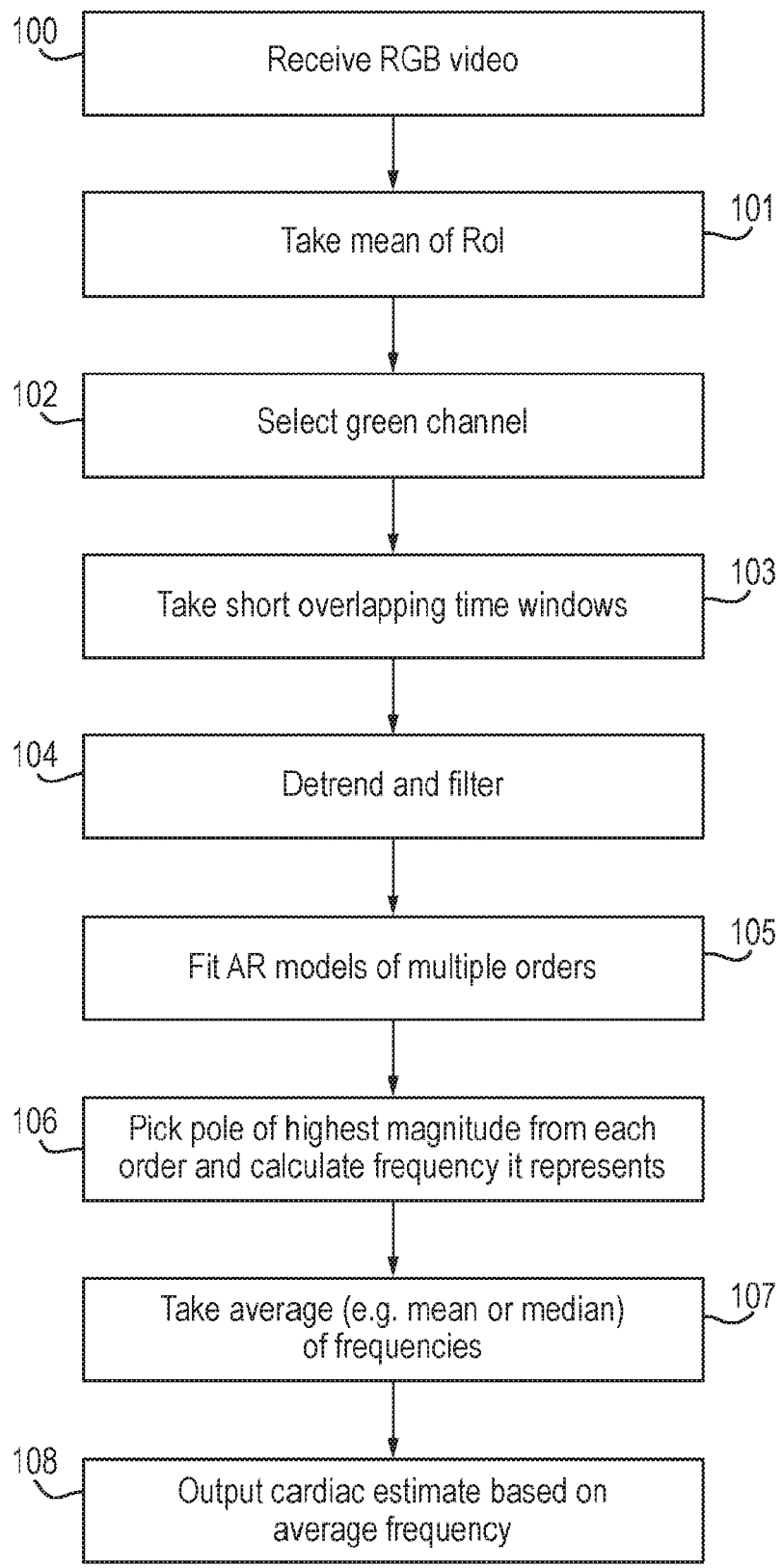
FIG. 1 is a flowchart explaining a prior art method of physiological signal analysis.

In the prior art method of FIG. 1 the dominant pole from each order model would be taken and the frequencies to which they correspond are averaged to provide an estimate of the periodic physiological signal. However in accordance with the invention, in this embodiment one or more of the poles from each of the models of different order are taken and in step 38 the frequency which they represent (i.e. their phase angle) is calculated. In step 40 a pure sinusoid of that frequency is generated, this sinusoid being of the same time length as the detrended and filtered ratio signal and with an amplitude proportional to the standard deviation of the detrended and filtered signal from step 34.

Then in step 42 the detrended and filtered component from step 34 is cross-correlated with the synthesised signal to find the coefficient of correlation c, this being repeated for all possible non-identical phase differences. In this repetition the synthesised signal may be moved relative to the ratio signal by one sample step each time, or a larger step can be used. Whichever phase difference gives the highest cross-correlation c is taken as the best fit for that model order. This procedure is repeated for poles from each of the different model orders. In step 44 the pole with the largest cross-correlation coefficient c is retained.

Steps 40, 42 and 44 can be conducted for only the dominant pole for each model order (i.e. the pole with the largest magnitude, possibly within an allowed frequency range for the physiological signal of interest), or it can be repeated for all poles within the allowed frequency range, or all poles from the model. The fewer poles processed, the quicker the processing.

In step 46 the frequency of the synthetic signal with the highest cross-correlation with the original ratio signal is selected as the estimated frequency of the physiological signal and is outputted. The output is preferably presented as, for example, a heart rate in beats per minute or a respiration rate in breaths per minute (by calculating the frequency in Hz times 60).

Steps 42 and/or 44 may be supplemented by a check that the cross-correlation c is above a predetermined threshold. If the cross-correlation is not above the predetermined threshold then the frequency may not be selected. Alternatively step 46 can be supplemented by the step of checking the cross-correlation coefficient c of the selected frequency against the predetermined threshold and if it is less than the threshold then the estimate is not output. This avoids outputting an estimate based on a poor level of periodic information in the input signal.

FIG. 4 shows data at different steps for an estimation of heart rate from a webcam. Three channels of video data are captured using a webcam (in this case operating at 12 frames per second), by averaging (mean) the red, green and blue components of the pixels in a region of interest on the subject's forehead, the three channels being shown in FIG. 4A. The channels are normalised by dividing each value by the mean for that channel for the whole time window (8 seconds in the illustrated example), resulting in the plots shown in FIG. 4B, and ratios are then taken of each pair of channels as shown in FIG. 4C. Principal Component Analysis is performed (resulting in the components shown in FIG. 4D) and the components are detrended and filtered resulting in FIG. 4E. For each principal component shown in FIG. 4E, the component with greatest "peakiness" in the frequency spectrum is chosen as the most periodic component. In this example the amplitude spectrum is calculated using the Fast Fourier Transform and the peak of the spectrum is found (marked with an arrow in FIG. 4F). The "peakiness" of the spectrum (which is used as a measure of periodicity) is calculated as the squared height of this peak divided by the area underneath the amplitude curve. In this example, the first principal component has the highest "peakiness" and hence the greatest periodicity. This component with greatest "peakiness" in the frequency spectrum is chosen as the most periodic component and autoregressive models of different orders are fitted to this component. Each of the pole frequencies from the autoregressive models is tested by calculating the maximum cross-correlation of a sinusoid at that frequency with the detrended, filtered component (FIG. 4G). Pole frequencies from all autoregressive model orders are tested, provided that the frequency is in the expected physiological range of heart rates. In this example, the highest cross-correlation was obtained for a frequency of 84 beats per minute, shown as a circle (which is from a pole of an autoregressive model with order 9). An estimated heart rate of 84 beats per minute is therefore outputted. This matches a simultaneous reference measurement of 84 beats per minute which was obtained from a finger pulse oximeter.

The invention claimed is:

1. A method of detecting the frequency of a periodic physiological signal of a subject from a video image of the subject, comprising the steps of:
   fitting autoregressive models of one or more orders to a sign derived from the video image to detect spectral components in the signal;
   for each spectral component generating a synthetic signal of the same frequency and calculating its similarity in the time domain with the signal derived from the video image;
   outputting as the physiological signal frequency the frequency of the synthetic signal with the maximum similarity with the signal derived from the video image.

2. A method according to claim 1 wherein the measure of similarity is cross-correlation.

3. A method according to claim 1 wherein the synthetic signal is sinusoidal.

4. A method according to claim 1, further comprising the step of defining a similarity threshold and inhibiting the outputting step if the similarity of the synthetic signal with the maximum similarity with the signal derived from the video image is below the threshold.

5. A method according to claim 1 wherein the signal derived from the video image is a single colour channel of video source data.

6. A method according, to claim 1 wherein the signal derived from the video image is a sequence of co-ordinates obtained by tracking physical movement in the image.

7. A method according to claim 1, wherein the signal derived from the video image is a ratio of two colour channels of video source data.

8. A method according to claim 1, wherein the signal derived from the video image is a sequence of co-ordinates of a physical feature being tracked.

9. A method according to claim 1, wherein the signal derived from the video image is derived by the following steps:

receiving multiple colour channels of video source data representing said video image, each channel comprising a time series of intensity data for that colour channel;

for each different pairing of the colour channels calculating the ratio of the intensity at each time point in a first of the pairing to the intensity at the same time point in the second of the pairing to produce multiple ratio signals;

performing source separation on the ratio signals and selecting the output component which is most periodic.

10. A method according to claim 1, wherein the signal derived from the video image is derived by the following steps:

receiving multiple sequences of co-ordinates of one or more physical features being tracked;

performing source separation on to sequences and selecting the output component which is most periodic.

11. A method according to claim 9 wherein the source separation is by Principal Component Analysis.

12. A method according to claim 9 wherein the selection of the most periodic output component is by selecting the component having the greatest peakiness of frequency spectrum.

13. A method according to claim 1 wherein autoregressive models of order 7 to 11 are fitted to the signal derived from the video image.

14. A method according to claim 1 wherein a synthetic signal is generated corresponding to the frequency of only the dominant spectral component for each order model.

15. A method according to claim 9 wherein the colour channels are red, green and blue and the pairings are red and green, red and blue, green and blue.

16. A method according to claim 7 wherein each colour channel is normalised by dividing by its mean before the step of calculating the ratio.

17. A method according to claim 1 wherein the signal derived from the video image is temporally windowed.

18. A method according to claim 17 wherein the signal derived from the video image is temporally windowed into overlapping windows.

19. A method according, to claim 18 wherein the windows are from 4-30 seconds long and the overlap is from 0.5 to 10 seconds.

20. A method according to claim 1 wherein the video source data is a time series of intensity data for each colour channel for a region of interest defined in the video image.

21. A method according to claim 20 wherein the region of interest is on the skin of the subject and the video source data is a photoplethysmographic image.

22. A method according to claim 20 wherein the region of interest includes a periodically moving part of subject.

23. A method according to claim 1 wherein the periodic physiological signal is the heart rate or respiration rate of the subject.

24. A non-transitory computer readable medium storing a computer program comprising a program code that causes a computer system to perform the method of claim 1.

25. Apparatus for detecting the frequency of a periodic physiological signal of a subject from a video image of the subject comprising:

an input for receiving one or more colour channels of video source data representing said video image, each channel comprising a time series of intensity data for that colour channel;

a processor for processing video source data;

the processor being configured to execute the steps of claim 1; the apparatus further comprising an output to output as the physiological signal frequency the frequency of the synthetic signal with the maximum cross-correlation with the selected ratio signal.

* * * * *